(12) United States Patent
Bajpai et al.

(10) Patent No.: US 10,806,179 B2
(45) Date of Patent: Oct. 20, 2020

(54) PORTABLE ELECTRONIC VAPORIZER

(71) Applicant: Puff Corp., Brooklyn, NY (US)

(72) Inventors: Avi Bajpai, New York, NY (US);
Roger Volodarsky, New York, NY (US)

(73) Assignee: PUFF CORPORATION, Los Angeles, CA (US)

( * ) Notice: Subject to any disclaimer, the term of this patent is extended or adjusted under 35 U.S.C. 154(b) by 328 days.

(21) Appl. No.: 15/487,145

(22) Filed: Apr. 13, 2017

(65) Prior Publication Data

US 2017/0295845 A1    Oct. 19, 2017

Related U.S. Application Data

(60) Provisional application No. 62/322,189, filed on Apr. 13, 2016.

(51) Int. Cl.
*A24F 47/00*   (2020.01)
*A61M 11/04*   (2006.01)
*A61M 15/06*   (2006.01)

(52) U.S. Cl.
CPC ......... *A24F 47/008* (2013.01); *A61M 11/042* (2014.02); *A61M 15/06* (2013.01); *A61M 2205/8206* (2013.01)

(58) Field of Classification Search
CPC ... A61M 15/06; A61M 11/042; A24F 47/002; A24F 47/008; A24F 2700/08; A24F 47/004; A24F 47/006
See application file for complete search history.

(56) References Cited

U.S. PATENT DOCUMENTS

| | | | |
|---|---|---|---|
| 2013/0152922 A1* | 6/2013 | Benassayag | A61M 15/06 128/202.21 |
| 2014/0000638 A1 | 1/2014 | Sebastian et al. | |
| 2014/0041655 A1 | 2/2014 | Barron et al. | |
| 2014/0186015 A1* | 7/2014 | Breiwa, III | A24F 47/004 392/386 |
| 2015/0068542 A1* | 3/2015 | Chang | A24F 47/008 131/328 |
| 2015/0090256 A1* | 4/2015 | Chung | A61M 15/002 128/202.21 |
| 2015/0128976 A1 | 5/2015 | Verleur et al. | |
| 2015/0257447 A1* | 9/2015 | Sullivan | A24F 47/008 131/329 |
| 2017/0086506 A1* | 3/2017 | Rado | A24F 47/008 |
| 2018/0125117 A1* | 5/2018 | DeMeritt | A24F 47/008 |

OTHER PUBLICATIONS

Patent Cooperation Treaty, International Search Report for PCT/US2017/027440, 3 pages Aug. 29, 2017.

(Continued)

*Primary Examiner* — Timothy A Stanis
*Assistant Examiner* — Cana A Gallegos
(74) *Attorney, Agent, or Firm* — Bryan Cave Leighton Paisner LLP

(57) ABSTRACT

A portable electronic vaporizer for vaporizing product to be inhaled by a user of the vaporizer. The portable electronic vaporizer includes a mouthpiece, a product chamber, a heating element, a power source, and a mouthpiece.

23 Claims, 12 Drawing Sheets

(56) References Cited

OTHER PUBLICATIONS

Puff Co., Puffco Pro, retrieved from web.archive.org/web/20141213054843/https://www.puffco.com/products/puffco-pro Jan. 1, 2015.
Kandy Pens, Gravity Quartz Crystal Atomizer, retreived from web.archive.org/web/20160430003435/https://www.kandypens.com/gravity-quartz-crystal-atomizer.html Apr. 30, 2016.
Kandy Pens, Donuts Violaceous Atomizer, retrieved from web.archive.org/web/20150909153713/https://www.kandypens.com/donuts-ceramic-vaporizer-violaceous-atomizer.html Sep. 9, 2015.
The Vape Critic, blog written by Bud, The Atmos Kiln Wax Atomizer, retrieved from web.archive.org/web/20170606213043/https://www.vapecritic.com/atmos-kiln/ Jun. 6, 2016.
Pax Labs, Inc., web page of vaporizers, retrieved from www.paxvapor.com Nov. 1, 2016.
Pax Labs, Inc., Pax vaporizers, retrieved from web.archive.org/web/20150226110043/https://www.paxvapor.com/ Feb. 26, 2015.
Storks and Bickel, Crafty Vaporizer, retrieved from web.archive.org/web/20141102053919/http://www.vapornation.com/crafty-vaporizer.html Nov. 2, 2014.
Atmos Nation, LLC, Atmos Jewel Vaporizer, retrieved from web.archive.org/web/20151102094426/https://www.puffitup.com/Atmos-Jewel-p/atm.jew.htm Nov. 5, 2015.
Wilhelm, J., The Past, Present, and Future of Cannabis Oil Vaporizer Cartridges, Leafly, retrieved from www.leafly.com/news/strains-products/the-past-present-and-future-of-cannabis-oil-vaporizer-cartridges Feb. 21, 2018.
Puff Co., Puffco Plus Bowl Marketing Material, retrieved from www.instagram.com/p/BFg0tz7JWN-/ May 17, 2016.
Puff Co., Puffco Plus Applicator Marketing Material, retrieved from www.instagram.com/p/BFmQ7qZJWBn/ May 19, 2016.
Puff Co., Puffco Plus Applicator Solo Marketing Material, retrieved from www.instagram.com/p/BFjcxlvJWPj/ May 18, 2016.
Puff Co., Puffco Plus Bowl Marketing Material, retrieved from www.instagram.com/p/BFfNpIJpWK0/ May 16, 2016.
Puff Co., Puffco Plus Exploded View Marketing Material, retrieved from www.instagram.com/p/BFmupRUJWLI/ May 19, 2016.
Puff Co., Puffco Plus Applicator Video Marketing Material, retrieved from www.instagram.com/p/BFkOFi9JWC9/ May 18, 2016.

\* cited by examiner

PORTABLE ELECTRONIC VAPORIZER

CROSS-REFERENCE TO RELATED APPLICATIONS

This application contains subject matter related to and claims the benefit of U.S. Provisional Patent Application No. 62/322,189, filed on Apr. 13, 2016, the entire contents of which are incorporated herein by reference.

FIELD OF THE INVENTION

The present invention generally relates to a portable vapor delivery device, and more specifically, an electronic portable vaporizer device for delivery of inhalable substances.

BACKGROUND

Electronic vaporizers are common place and are generally utilized for the purpose of aroma and/or inhalation therapy. In this regard, vaporizers heat a substance, herbs for example, such as tobacco, cannabis, lavender, chamomile, and many other types of plant material.

The vaporizer may work by heating the substance through the use of direct heat or the use of hot air in one of three ways. The first is thermal conduction where the substance is set directly on a heating element such as a ceramic or metal plate. The second is thermal radiation in which light is used to heat the substance. The third is convection where hot air is passed over the substance.

At lower levels of heat, vapors extracted from vegetable materials are mainly aroma therapeutic (inactive fragrance) and do not usually contain the active ingredients of the substance. Without the active ingredients being present, there is no physiological reaction. At higher levels of heat, active ingredients will be included in the vapor given off during heating. Usually aromatic vapors have already been released and are not always present at the higher heat levels. With some substances, such as cannabis, active ingredients appear at different levels of heat.

After the substance is heated a mist or vapor containing some aspect of the substance is released and either enjoyed as an aromatic or inhaled to obtain a physiological reaction. The warm air containing the substance product can be harsh on the throat and bronchial tubes. Accordingly, some vaporizers use a cooling down process that allows water moisture to be included in the vapor produced. These vaporizers enable the user to inhale a cool moist vapor that is relatively less harsh and irritating.

Vaporizers are often preferred over traditional methods of heating or smoking substances due to the reduction of harsh side effects. Some of these side effects include inhalation of tar, carbon monoxide, and other carcinogens either directly or from second hand smoke. With many states imposing smoking bans in public areas, vaporizers have become popular substitutes.

As indicated above, vaporizers work by heating a substance to extract a product of the substance, which is typically facilitated by the use of butane, open flame, or electricity.

SUMMARY

Among the various aspects of the present disclosure is the provision of a portable vaporizer as substantially shown and described.

In one aspect, a portable vaporizer device includes a first housing extending along a longitudinal axis. The first housing has a first end and a second end, and is at least partially hollow so as to define a first cavity between the first end and the second end. The first end has a first opening with an interior edge in fluid communication with the cavity. A product chamber includes a base and one or more upstanding walls. A bowl is located in the product chamber. The portable vaporizer device further includes a heating element and a power source. A mouthpiece is formed from a second housing and extends along the longitudinal axis. The second housing has a first end and a second end, wherein the first end of the second housing is detachably connected.

Other objects and features will be in part apparent and in part pointed out hereinafter.

DETAILED DESCRIPTION

Figure 1:
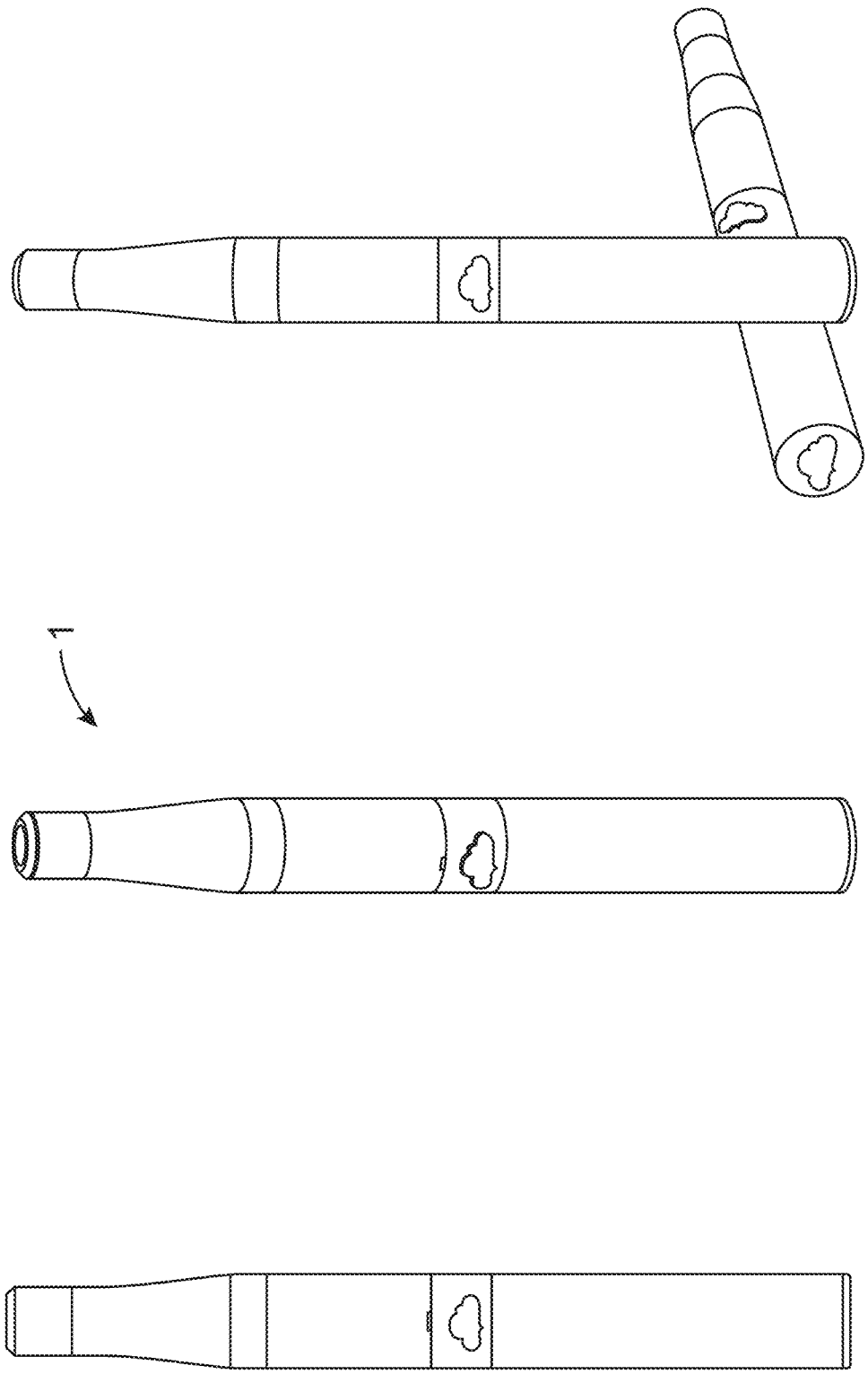
FIG. 1 shows two views of an embodiment of the electronic vaporizer device according to the present invention.
Figure 2:
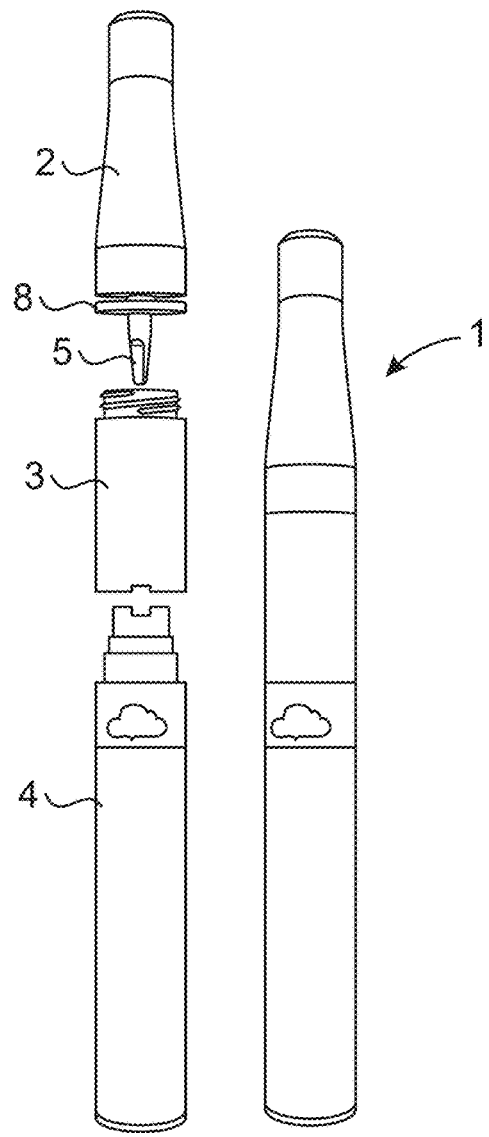
FIG. 2 is an exploded view of embodiment of the electronic vaporizer device which shows the applicator means attached to the mouthpiece.

Referring now to FIG. 1, an embodiment of the portable electronic vaporizer device (1) is shown in drawings and renderings. FIG. 2 is an exploded rendering of the vaporizer device, showing a mouthpiece (2), a product chamber (also referred to herein as an atomizer) (3) and a first housing (4). A battery component is located in the first housing (4). Removably secured within the mouthpiece (2) is an applicator means (5) and a convection cap (8).

In one embodiment, the first housing has a hollow portion adapted to hold a battery (not shown). The battery component may be adapted to accept one or more batteries. Preferably, the battery component is comprised of a housing that has a hollow portion adapted to hold a battery. The battery component may be adapted to accept one or more batteries. Also, the battery component may be adapted to accept a non-rechargeable battery or a rechargeable battery. The battery component may have a door or other means to allow a battery to be inserted into and removed from the battery component. It is understood that other battery component configurations are within the scope of the present invention.

If the battery component is designed to accept a rechargeable battery, the battery component may have a charging port connectable to a battery charger. The charging port would be in electric communication with a battery in the battery component. A battery charger may be connectable to a source of electricity (e.g., a wall outlet or a computer) and connected to the charging port to charge the rechargeable battery. Rechargeable batteries and means for charging them are well known in the art.

The other end of the battery component may include a light that is activated when the portable vaporizer is used as described herein. For example, the light may signal that the vaporizer is in use, as well as the temperature or heating level that may be selected by the user.

The mouthpiece component (2) is formed from a hollow housing with a first opening (7) and a second opening that is removably attached to the product chamber (3).

The portable vaporizer (1) may have a button or other means of operating the device. In the present drawings, the button is shown as a cloud-shaped logo on the first housing. In use, when the button is depressed, an internal circuit connecting the battery and the heating element is completed, allowing electricity to pass through the heating element (13). The resistance of the heating element causes the heating element to heat the bowl. Oil or wax placed into the bowl may be vaporized by the heat of the bowl.

The button may be formed of a transparent or translucent material, and may preferably be silicone or plastic. The button may also allow a user to select from different levels of available current to pass through the heating element, thereby allowing different temperatures. The button may also allow for continuous current to pass through the heating element, thereby allowing the entire contents of the bowl to be vaporized with a single press of the button. The button may also be used to lock and unlock the vaporizer. In a locked stated, pressing the button would not activate the heating element, while in an unlocked state, pressing the button would activate the heating element.

Figure 3:
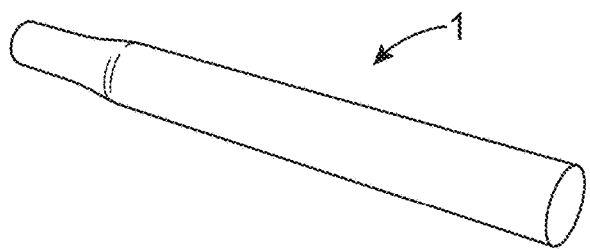
FIG. 3 is a perspective view of the electronic vaporizer device according to the present invention.
Figure 4:
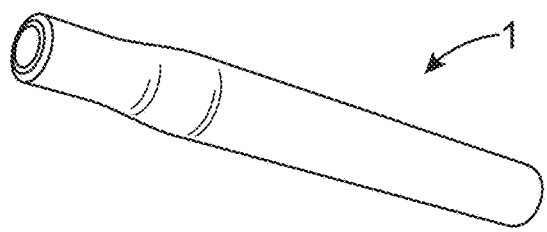
FIG. 4 is a front perspective view of the electronic vaporizer device according to the present invention.

FIGS. 3 and 4 show perspective views of an embodiment of the portable electronic vaporizer device according to the present invention. In these views, the mouthpiece is mechanically connected to one end of the product chamber, and the first housing component is mechanically connected to another end of the product chamber.

Figure 5:
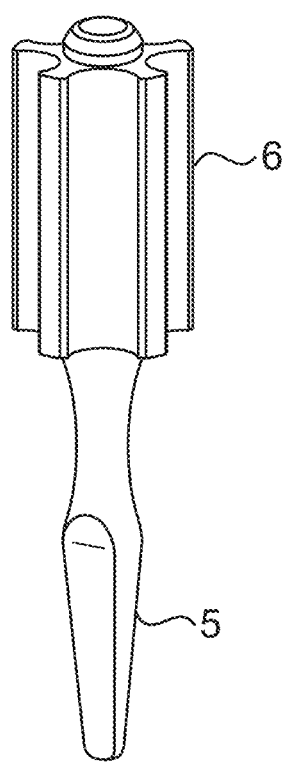
FIG. 5 is a perspective view of the applicator means and filter.

FIG. 5 is a close-up view of the applicator means (5) connected to a filter (6). When removably secured within the mouthpiece (2), the filter functions both to hold the applicator means in the mouthpiece and also to educe or eliminate any unwanted or undesirable contents from entering a user's mouth or accumulating inside the mouthpiece, which accumulation could restrict airflow.

Figure 6:
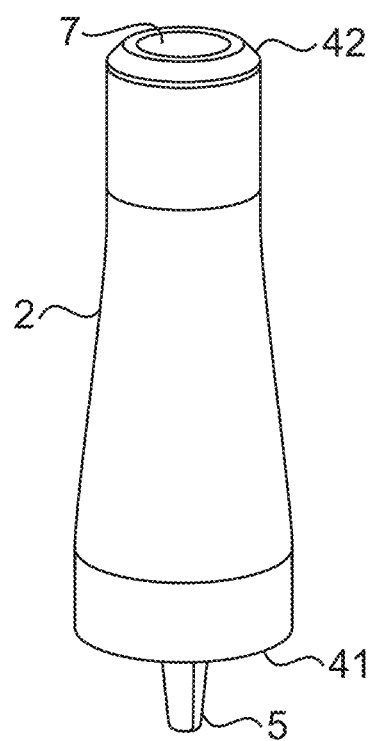
FIG. 6 is a perspective view of the applicator means and filter arranged within the mouthpiece.

FIG. 6 is a close-up exterior view of the mouthpiece (2). The applicator means (5) extends slightly beyond the edge of a first end (41) of the mouthpiece housing. The second end (42) of the mouthpiece (2) has a first opening (7) where vapor will exit the vaporizer device upon inhalation by a user.

Figure 7:
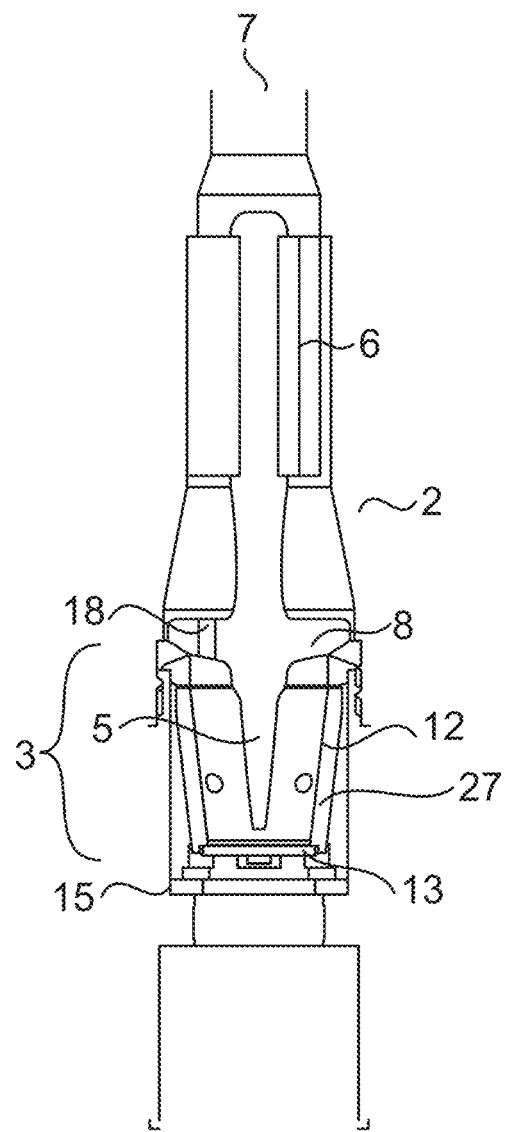
FIG. 7 is a schematic view showing the mouthpiece and atomizer parts according to the portable vaporizer device of the invention.

As shown in FIG. 7, the filter (6) is secured in the mouthpiece (2). A securing post (23) is secured removably in an axial, hollow opening (6A) in the filter (6). A convection cap (8) is affixed to the securing post, and below the convection cap is the applicator means (5). The securing post (23), convection cap (8) and applicator means (5) can together be formed as a single object or, alternatively, separate objects which may be fixedly or removably attached to each other.

When the mouthpiece (2) is attached to the product chamber (3), the applicator means will be suspended within the bowl (12). The bowl (12) is preferably made of ceramic or a ceramic blend or composite. The bowl (12) can be any shape, but is preferably rounded with upstanding wall or walls (27) surrounding a base. The base of the bowl also functions as the heat source for the atomizer, as the base comprises a heating plate (13). The heating plate is heated to a desired temperature, preferably greater than 300 degrees Fahrenheit, by any well-known means.

In an embodiment, the product chamber (3), also referred to herein as the atomizer or atomizer component, comprises a housing with circumferential walls. One end of the product chamber may be mechanically attachable to one end of the first housing and battery component. The product chamber may be attached to the first housing and battery component by screw threads on the battery component, which may be mated to screw threads on the atomizer component. Other means for connecting these parts known in the art include snapping the parts together or using magnets. In an alternative embodiment, the product chamber and first housing can be combined into a single housing.

Furthermore, this figure shows that the product chamber may contain a cavity, wherein a bowl (12) is located. The cavity may have a base and circumferential walls. The bowl is preferably shaped as a cup with a base and circumferential having a cylindrical cross-section. The exterior of the bowl may be of the same shape and dimensions as the interior walls of the cavity or different shape and different dimensions. In addition, the height of the walls of the bowl may be lower than the height of the walls of the cavity. The internal volume of the bowl may be, for example, over 2 cubic centimeters. In a preferred embodiment, the bowl is made from a ceramic material.

To secure the bowl in the housing of the product chamber, a retaining element (30), which is preferably shaped as a ring, may be fitted at the open end of the product chamber cavity. The retaining element (30) may have at least one opening through which the product to be vaporized can be inserted into the bowl (12). The retaining element is preferably made of stainless steel, but can be made of any suitable component including glass, ceramic or other metal. The use of the retaining element eliminates the need for glue, plastics or other adhesives to secure the components of the product chamber, and thereby eliminates the risk that glue or other adhesives may be vaporized from the heat emanating from the heating element, and the risk of fumes from glue or adhesives being inhaled with the product vapors when the user inhales the product vapors.

A heating element (13) is preferably disposed within the product chamber and forms the base of the bowl. The heating element may be a heating plate or wire-wrapped ceramic post. Preferably, the heating element is a flat heating plate that does not include or require exposed heating coils. The heating element is electrically connected to a battery in the first housing. For example, the heating element may be electrically connected to the battery by a wire or direct connection.

Figure 8:
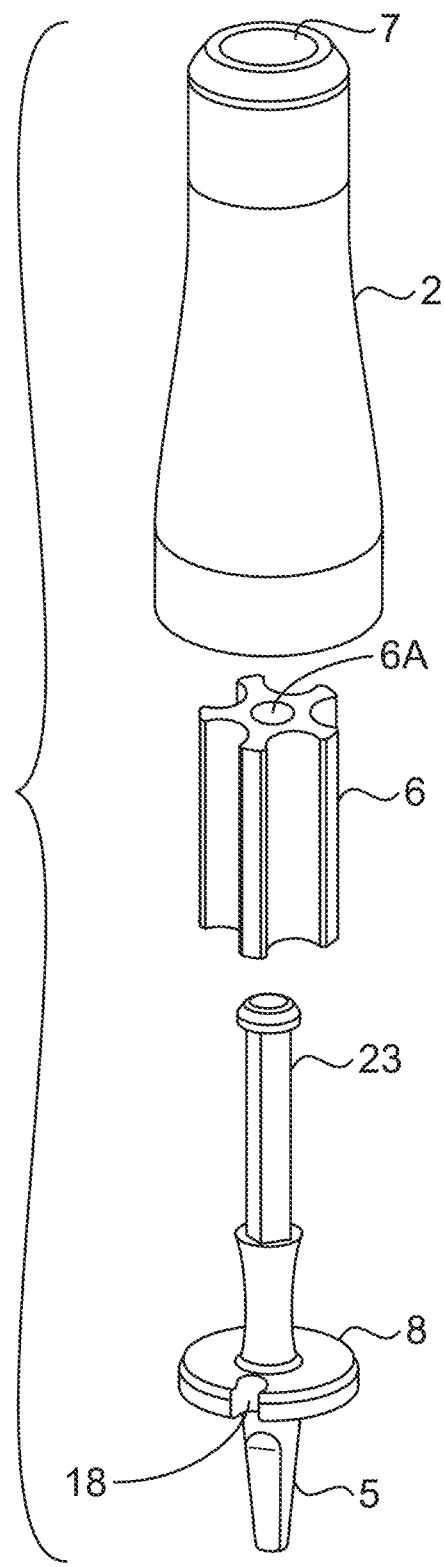
FIG. 8 is an exploded view of the applicator means, convection cap, filter, and mouthpiece.

FIG. 8 is an exploded diagram of the mouthpiece (2). In the embodiment shown herein, the securing post (23), convection cap (8) and applicator means (5) are a continuous, single piece.

Figure 9:
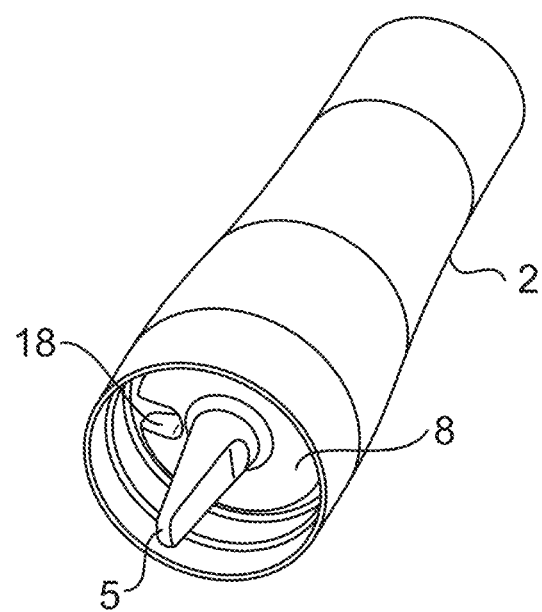
FIG. 9 is a perspective view of the mouthpiece.
Figure 10:
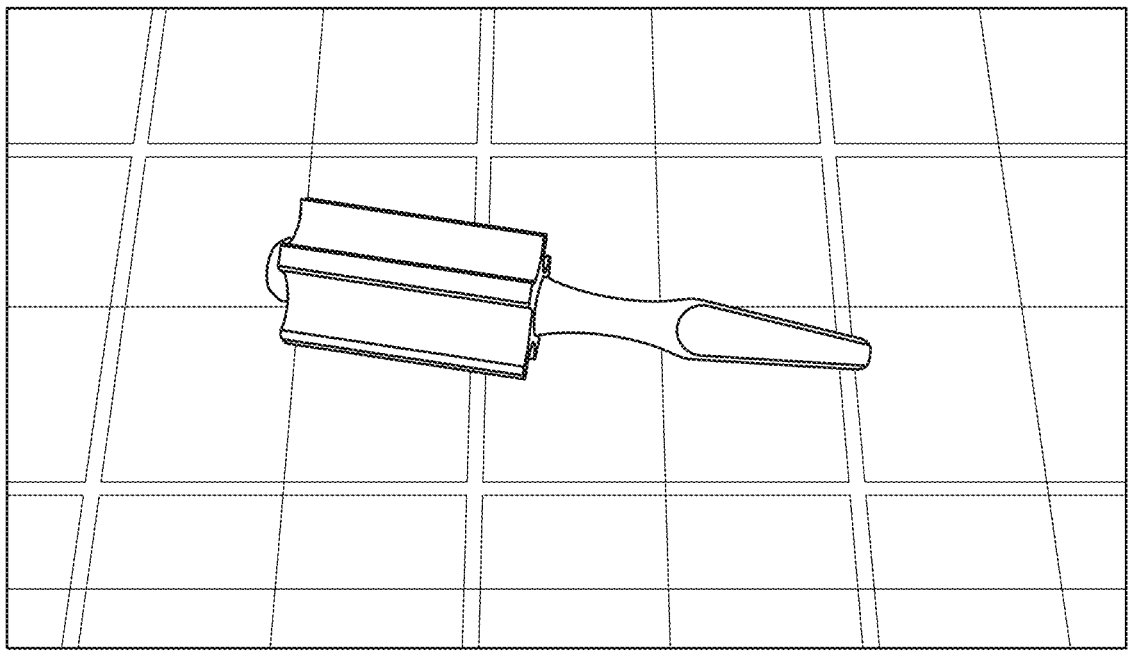
FIG. 10 shows a rendering of the filter and applicator means.
Figure 11:
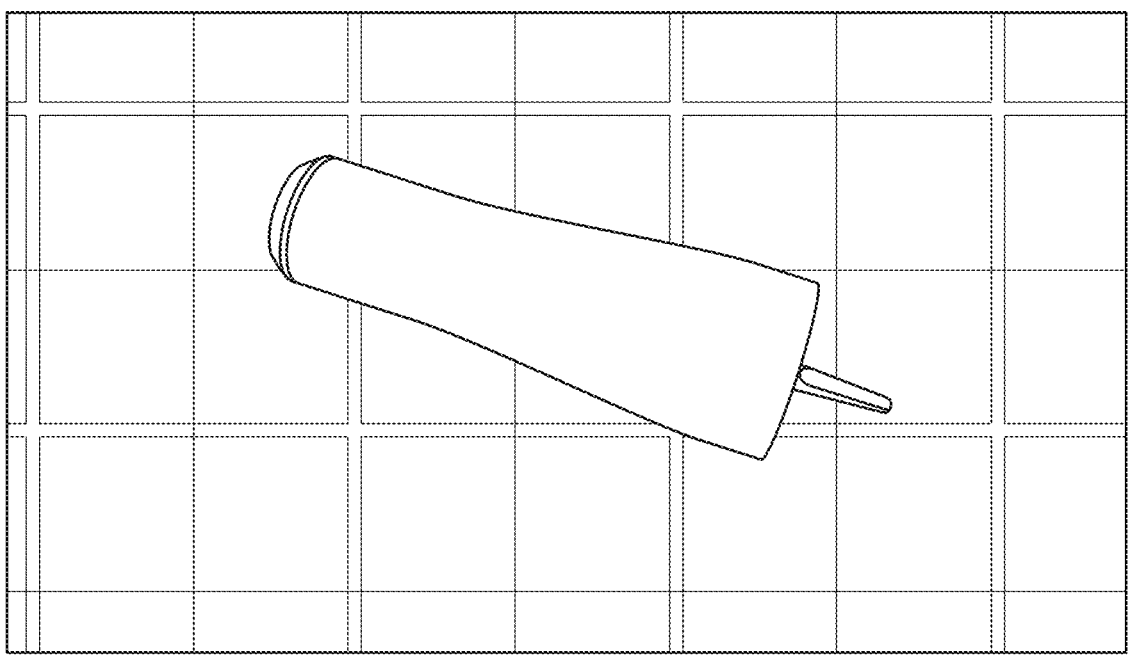
FIG. 11 shows a rendering of the mouthpiece and applicator means.
Figure 12:
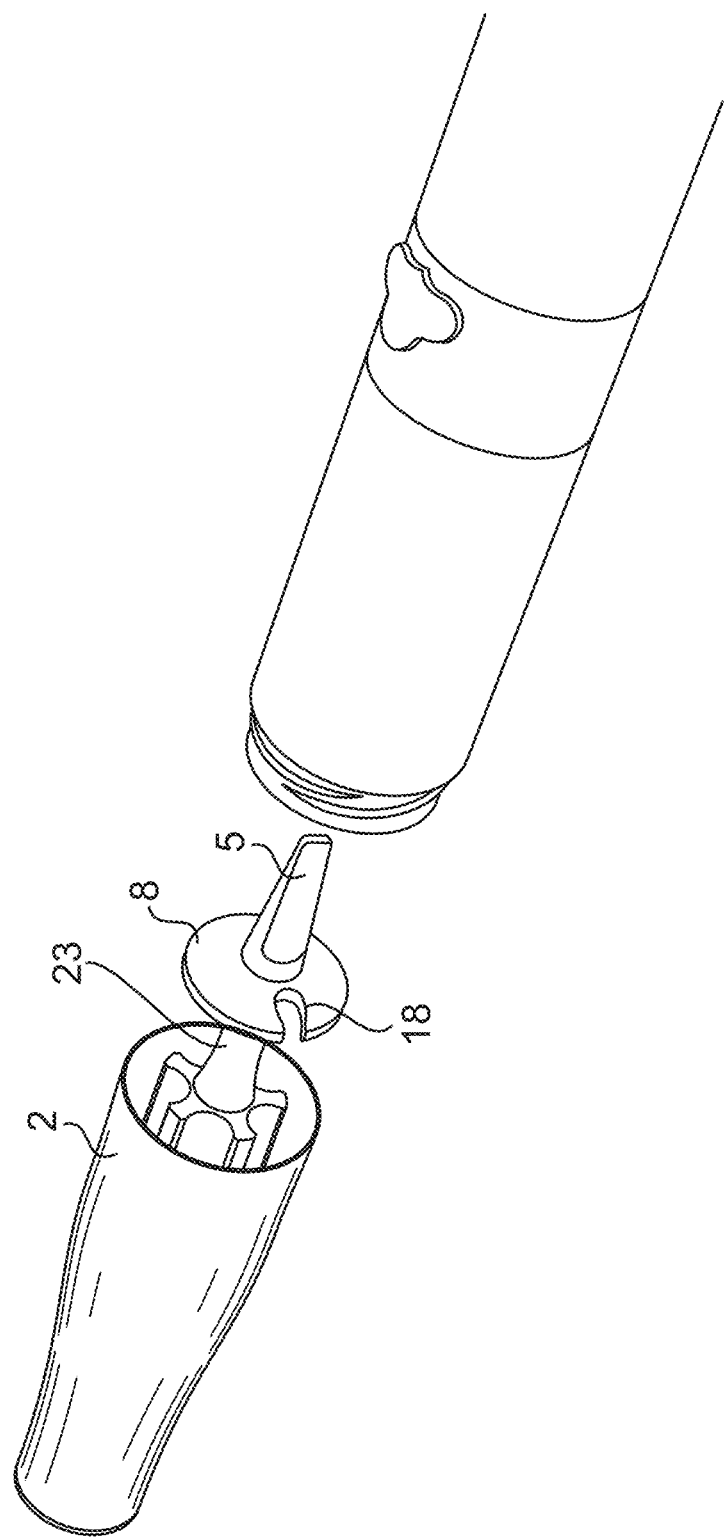
FIG. 12 is a partially exploded rendering of the portable electronic vaporizer according to the present invention.

FIG. 9 is a perspective view of the mouthpiece (2), which shows the convection cap (8) and application means (5) positioned in the housing. The convection cap (8) may form a seal with the inner walls of the mouthpiece housing, whereby the vapor is directed through an aperture (18) located in the convection cap (8).

Figure 13:
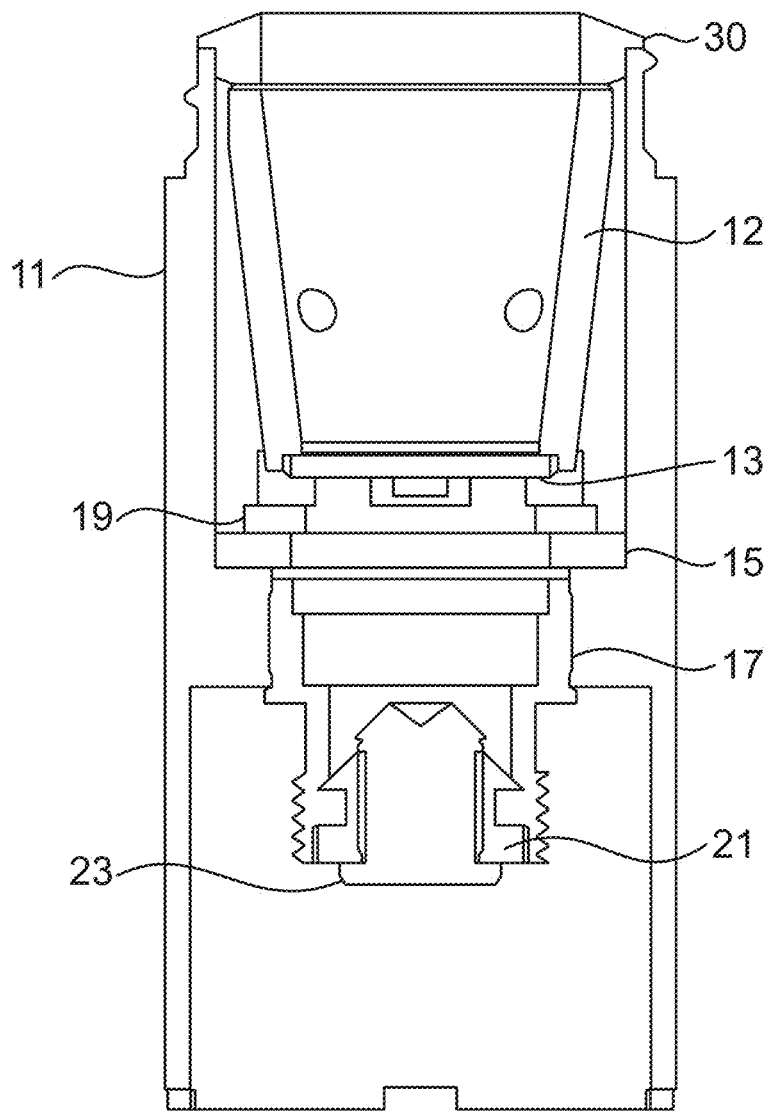
FIG. 13 is a schematic diagram of the atomizer according to an embodiment of the present invention.
Figure 14:
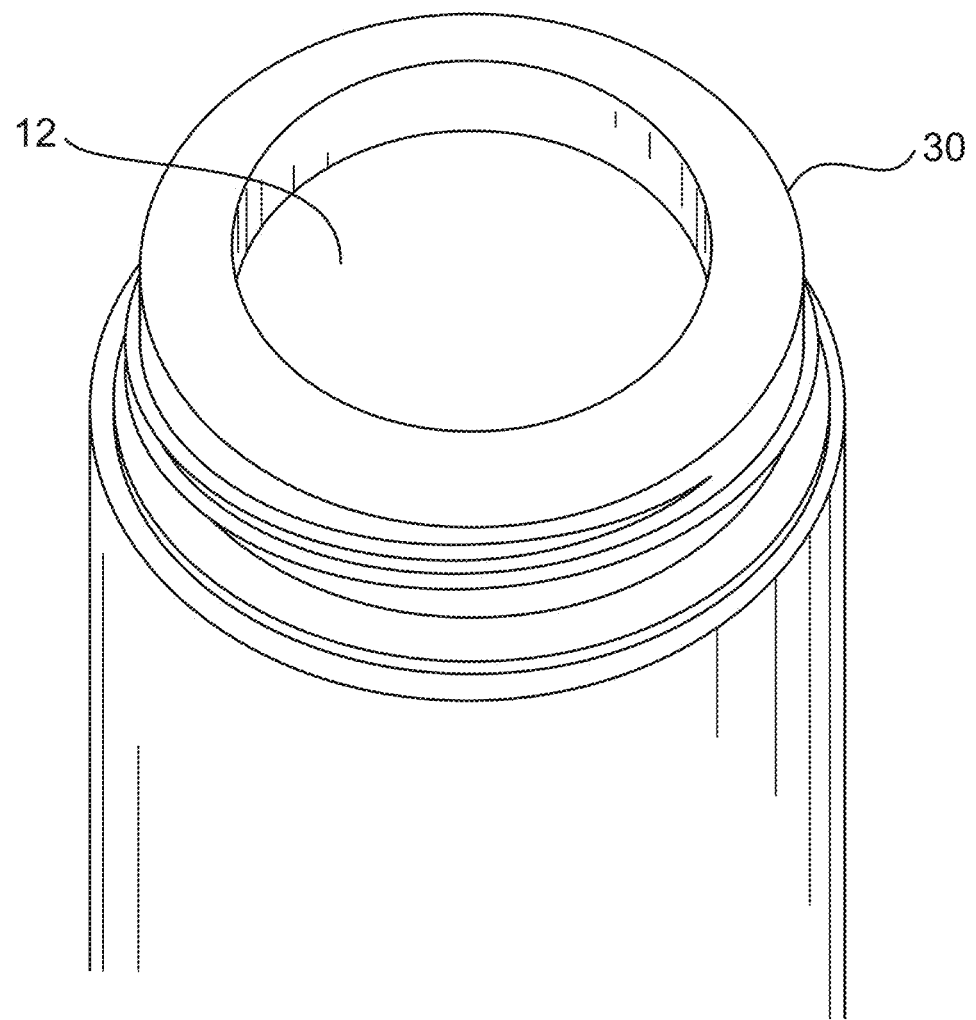
FIG. 14 is a rendering showing a front perspective view of the atomizer according to an embodiment of the present invention.
Figure 15:
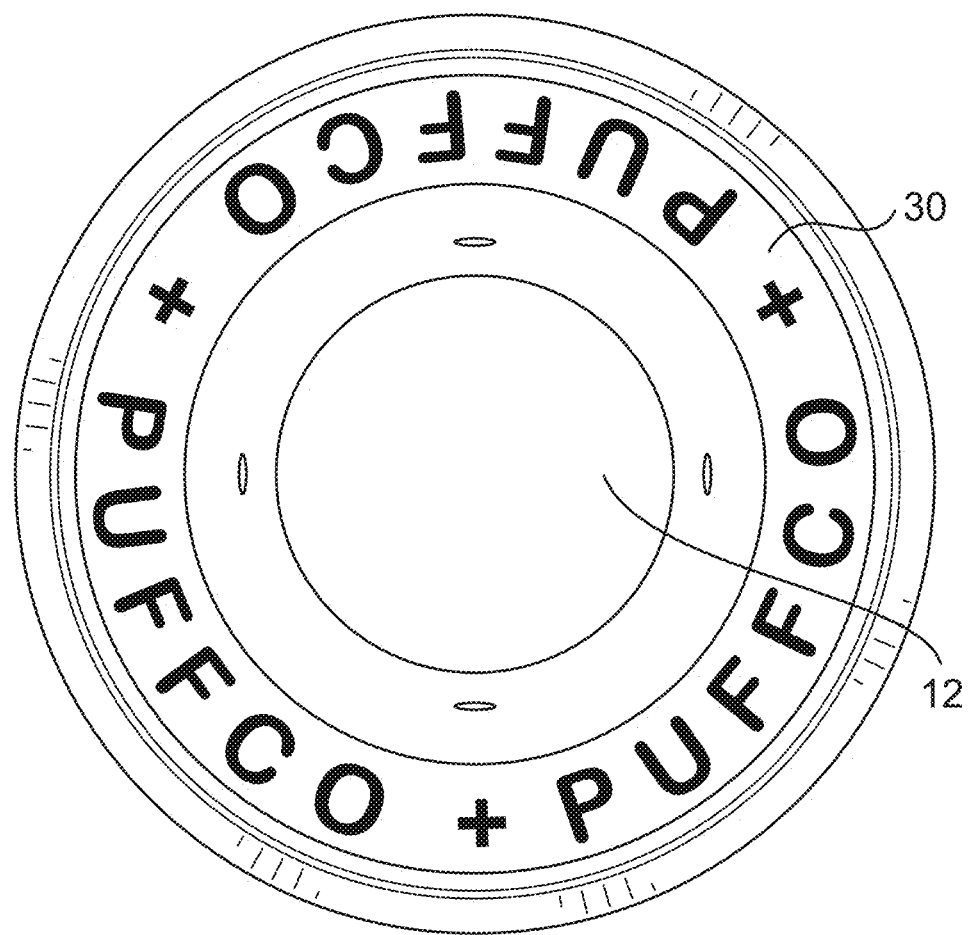
FIG. 15 is a rendering showing a plan view of the atomizer according to an embodiment of the present invention.

FIG. 13 shows a close-up schematic of the product chamber housing (11), also referred to herein as the atomizer housing. In a preferred embodiment, a securing ring (30) is fitted on the edge of the top of the product chamber. FIG. 13 further depicts silicone washer 15 (also shown in FIG. 7), spacer 19, airflow insert 17, grommet 21 and connector pin 23.

The Applicator

In order to load oil or wax into a vaporizer, some users will use a specialized tool, commonly called a "dabber" in the art, to remove the oil or wax from a substrate or container and transfer the oil or wax into the vaporizer bowl prior to vaporization. Until now, these applicators have been separate tools, and not secured in any way to the vaporizer. Given an applicator's small size, they are easily lost or misplaced, and can even be difficult to manipulate for some users. Therefore, there is a need in the art for a vaporizer with an integrated "dabber" or applicator.

In an embodiment of the present invention, the portable electronic vaporizer device contains an applicator removably secured within the mouthpiece for applying or loading oil or wax into the bowl prior to vaporization. This applicator can be any shape suitable for removing oil or wax from a first surface or container and transferring it to the vaporizer bowl. Preferably, the applicator is flat, semi-flat, shovel-like, spade shaped, or any other suitable shape in order to efficiently transfer oil or wax from a substrate into the vaporizer bowl. More preferably, the applicator is tapered from the end removably secured in the mouthpiece toward the opposite end.

The applicator according to the present invention is preferably comprised of plastic, ceramic, glass or metal, though other suitable materials are within the scope of the present invention.

The Convection Cap

The portable electronic vaporizer according to the present invention also preferably includes a cap or valve located in the cavity of the mouthpiece. The cap contains an aperture or a plurality of apertures in the cap to allow vapor and air flow through the mouthpiece during inhalation. One of the benefits of the cap is that it allows for turbulent flow of air within the bowl during inhalation. This also allows for convective heating in the bowl, in addition to the conductive heating from the heating element. Additionally, the convection cap may also prevent "splashing" of liquefied oil into the mouthpiece and reduces condensation of vapor in the mouthpiece.

The convection cap is preferably round, but can be any shape such that the cap fits in the cavity of the mouthpiece thereby restricting vapor and air flow primarily through the aperture in the cap.

Preferably, the convection cap is made of ceramic, plastic, metal or glass. More preferably, the convection cap comprises ceramic. Other configurations are within the scope of the present invention.

The Bowl

Prior art product chambers or atomizers typically included a heating element located inside a bowl, wherein the heating element was made of a conductive material through which current passed causing the conductive material to heat up. Oil or wax product in the bowl frequently came into direct physical contact with the conductive material. This could cause the oil or wax to char instead of vaporize, thereby creating a "burnt" taste for the user, and also increased waste of product. Therefore, there is a need for an improved heating and vaporization process that reduces waste and charring of vaporizable material and which does not include exposed conductive materials.

Accordingly, an embodiment of the present invention solves the issues of prior art vaporizers by employing a bowl free of exposed conductive materials. This is accomplished by employing an atomizer consisting of an open ended bowl (12) and a heating plate (13) formed to fit in to the bottom of the bowl, thereby sealing the bowl or chamber from the bottom. The bowl (12) is made of ceramic or glass material, and the heating plate is made of a conductive material encased in ceramic or glass material. The result is an atomizer bowl with a heated bottom surface free of exposed conductive material. The seal created between the inner walls of the bowl (12) and the heating plate (13) is due to the pressing of the securing ring (30) in to the atomizer housing (11), stacking the bowl and heating plate and sealing them firmly together. The vaporizer according to the present invention creates vapor by heating the wax or oil substance through thermal conduction and/or by thermal convection. During the conductive heating of the wax or oil substance, the bowl (12) is heated, via the heating element (13), to an elevated temperature sufficient to vaporize the substance. The conductive heating of the bottom of the ceramic bowl also heats the surrounding air within the atomizer bowl, thereby creating a thermal convection within the bowl, which allows for more consistent temperature, and thereby more efficient vaporization of the oil or wax substance.

Use

To use the portable electronic vaporizer device described herein, a user first detaches the mouthpiece component from the product chamber, thereby exposing the applicator. The user then preferably uses the applicator to remove oil or wax product from a substrate and then loads the bowl located in the product chamber with the oil or wax. The user then reattaches the mouthpiece to the product chamber, and also reattaches the product chamber to the first housing, if not already attached. When ready, the user activates the heating element by pressing the button, thereby causing the heating element to heat the bowl. When the product has reached vaporization temperature, the user may inhale through the mouthpiece. When the user inhales, air travels through slots at the base of the product chamber. The air then travels through the airflow insert underneath the heating element, along the outer surface of the bowl and into the bowl through a plurality of air holes. Once in the bowl (12) the air mixes with vapor. The vapor then travels through the aperture (18) in the convection cap (8), up through the mouthpiece (2) and into the user's lungs.

It should be appreciated that the foregoing discussion related to the figures herein is illustrative only, and that the various embodiments of the disclosure may be implemented by any other appropriate system or method.

In the preceding specification, various preferred embodiments have been described with references to the accompanying drawings. It will, however, be evident that various modifications and changes may be made thereto, and additional embodiments may be implemented, without departing from the broader scope of the invention as set forth in the claims that follow. The specification and drawings are accordingly to be regarded as illustrative rather than restrictive.

We claim:

1. A portable vaporizer device comprising:
an atomizer chamber comprising:
an atomizer housing;
a bowl disposed within the atomizer housing that is configured to hold a vaporizable product therein, the bowl comprising:
one or more walls surrounding an interior of the bowl, the one or more walls forming a top opening and a bottom opening to the interior; and
a heating plate configured to seal and block air flow through the bottom opening of the one or more walls, and form a base portion of the bowl, the heating plate comprising a ceramic or glass material having a conductive material therein, and the heating plate comprising a surface that is configured to receive the vaporizable product, wherein the heating plate is configured to heat vaporizable product received on the surface of the heating plate and generate vapor therefrom, and
a retaining element configured to be fitted over the top opening of the one or more walls surrounding the interior of the bowl, to retain the bowl in the atomizer housing, and wherein the retaining element exerts a pressure on the one or more walls surrounding the interior of the bowl to seal the one or more walls to the heating plate
a removably attachable mouthpiece, the mouthpiece comprising a mouthpiece housing having a first inhalation opening, and a second opening that is adapted to receive vapor generated by conductively heating the vaporizable product within the atomizer.

2. The portable vaporizer device according to claim 1, wherein the heating plate comprises the conductive material encased in the ceramic or glass material, and the one or more walls are also formed of a ceramic or glass material. .

3. The portable vaporizer device according to claim 1, wherein the surface of the heating plate is free from exposed conductive material.

4. The portable vaporizer device according to claim 1 wherein the heating plate comprises a flat plate.

5. The portable vaporizer device according to claim 1, wherein the one or more walls surrounding the interior of the bowl form a seal with a periphery of the surface of the heating plate.

6. The portable vaporizer device according to claim 1 wherein the interior of the bowl has an internal volume of at least 2.1 cubic centimeters.

7. The portable vaporizer device of claim 1, wherein the retaining element is held in position by friction between the retaining element and the atomizer housing.

8. The portable vaporizer device according to claim 1, wherein the retaining element is ring-shaped.

9. The portable vaporizer device according to claim 8, wherein the ring-shaped retaining element comprises stainless steel.

10. The portable vaporizer device according to claim 1, further comprising:
a convection cap comprising one or more apertures therein and connected to a product applicator adapted to facilitate application of vaporizable product to the bowl, the convection cap being configured to be fitted over a top opening of the atomizer housing such that a flow of vapor out of the atomizer chamber is primarily through the one or more apertures,
wherein the product applicator extends from the convection cap and into an interior region of the bowl when the convection cap is fitted over the top opening of the atomizer housing.

11. The portable vaporizer device according to claim 10, wherein the product applicator is connected to the convection cap such that a distal end of the product applicator is suspended above a bottom surface of the bowl when the convection cap is fitted over the top opening of the atomizer housing.

12. The portable vaporizer device according to claim 10, wherein the convection cap and product applicator are removable from the device as a single object with one another.

13. The portable vaporizer device according to claim 12, wherein the convection cap and product applicator are formed as a single continuous piece.

14. The portable vaporizable device according to claim 12, wherein the convection cap and product applicator are removably attached to one another.

15. The portable vaporizer device according to claim 12, wherein the convection cap and product applicator are attached to the removably attachable mouthpiece, and wherein attachment of the mouthpiece to the atomizer housing causes the convection cap to be fitted over the top opening of the atomizer housing with the product applicator extending into the interior region of the bowl.

16. The portable vaporizer device according to claim 10, wherein the convection cap forms a seal with inner walls of the mouthpiece housing to restrict the flow of vapor into the mouthpiece from the atomizer chamber to primarily through the one or more apertures.

17. The portable vaporizer device according to claim 10, wherein the convection cap is configured such that fitting the convection cap over the top opening of the atomizer housing allows for a turbulent flow of air and/or vapor in the atomizer chamber.

18. The portable vaporizer device according to claim 10, wherein the bowl comprises one or more holes formed in sidewalls thereof to allow entry of air into the bowl in the atomizer chamber, and wherein the air flow into the bowl mixes with vapor inside the bowl and exits the atomizer chamber through the one or more apertures in the convection cap.

19. The portable vaporizer device according to claim 10, wherein the product applicator and convection cap are attached to a filter that is configured to be inserted at a location towards the first inhalation opening of the mouthpiece, the filter being configured to hold the product applicator and convection cap in place in the device via its insertion into the mouthpiece.

20. The portable vaporizer device according to claim 10, wherein the atomizer housing and mouthpiece housing are configured to be mechanically connected to one another, and wherein the convection cap is configured to be disposed interior to the atomizer housing and/or mouthpiece housing.

21. The portable vaporizer device according to claim 10 wherein the product applicator is attached to a securing post to which the convection cap is also attached at a point along the securing post that is above a distal end of the product applicator.

22. The portable vaporizer device according to claim 21, wherein the convection cap is attached to the securing post at a position along the securing post with respect to the distal end of the product applicator such that the distal end of the product applicator is suspended above a bottom surface of the bowl when the convection cap is fitted over the top opening of the atomizer housing.

23. The portable vaporizer device according to claim 10, wherein the product applicator comprises a single applicator tip.

\* \* \* \* \*